United States Patent
Mochii et al.

(10) Patent No.: US 9,304,109 B2
(45) Date of Patent: Apr. 5, 2016

(54) MAGNETIZING APPARATUS FOR MAGNETIC PARTICLE TESTING OF A WHEEL USING A CONDUCTOR AND AUXILIARY CONDUCTORS FOR MAGNETIZATION

(75) Inventors: Takashi Mochii, Yamatokoriyama (JP); Michitaka Hori, Tokorozawa (JP); Muneo Ishida, Kodaira (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 93 days.

(21) Appl. No.: 14/346,011

(22) PCT Filed: Aug. 8, 2012

(86) PCT No.: PCT/JP2012/070160
§ 371 (c)(1),
(2), (4) Date: Jul. 2, 2014

(87) PCT Pub. No.: WO2013/046944
PCT Pub. Date: Apr. 4, 2013

(65) Prior Publication Data
US 2014/0306699 A1   Oct. 16, 2014

(30) Foreign Application Priority Data
Sep. 26, 2011 (JP) .................. 2011-208707

(51) Int. Cl.
*G01N 27/82* (2006.01)
*G01N 27/84* (2006.01)
*B60B 17/00* (2006.01)
*H01F 7/20* (2006.01)

(52) U.S. Cl.
CPC ............ *G01N 27/82* (2013.01); *B60B 17/00* (2013.01); *G01N 27/84* (2013.01); *H01F 7/20* (2013.01)

(58) Field of Classification Search
CPC .......... B60B 17/00; G01N 27/82; G01N 27/84; H01F 7/20
USPC .......................................... 324/228, 239–243
See application file for complete search history.

(56) References Cited

U.S. PATENT DOCUMENTS 3,693,075 A * 9/1972 Forster ................... G01B 7/10
                                                                    324/220
3,825,822 A * 7/1974 Forster ............... G01N 27/9033
                                                                    209/570
5,610,517 A * 3/1997 Ma ...................... G01N 27/9046
                                                                    324/220

FOREIGN PATENT DOCUMENTS

| JP | 55-165266 | 11/1980 |
| JP | 60-165543 | 8/1985 |
| JP | 62-25253 | 2/1987 |

(Continued)

*Primary Examiner* — Jay Patidar
(74) *Attorney, Agent, or Firm* — Clark & Brody

(57) ABSTRACT

The present inventions provides a magnetizing apparatus 100 for magnetic particle testing of a wheel 7 that includes a hub 71, a plate 72, and a rim 73 in sequence from inward to outward in a radial direction of the wheel. The apparatus includes: a conductor 1 inserted through a bore 711 of the hub 71; and a pair of auxiliary conductors 2 connected to respective opposite end portions of the conductor 1, and so disposed as to face respective opposite side surfaces of the wheel 7, and to extend from the hub 71 to the rim 73 outwardly in a radial direction of the wheel 7, wherein the pair of auxiliary conductors 2 and the conductor 1 are energized with alternating current.

2 Claims, 3 Drawing Sheets

(56) References Cited

FOREIGN PATENT DOCUMENTS

| | | |
|---|---|---|
| JP | 01-299455 | 12/1989 |
| JP | 04-361153 | 12/1992 |
| JP | 07-103942 | 4/1995 |
| JP | 2003-344359 | 12/2003 |
| JP | 2010-083470 | 4/2010 |

* cited by examiner

Figure 2A

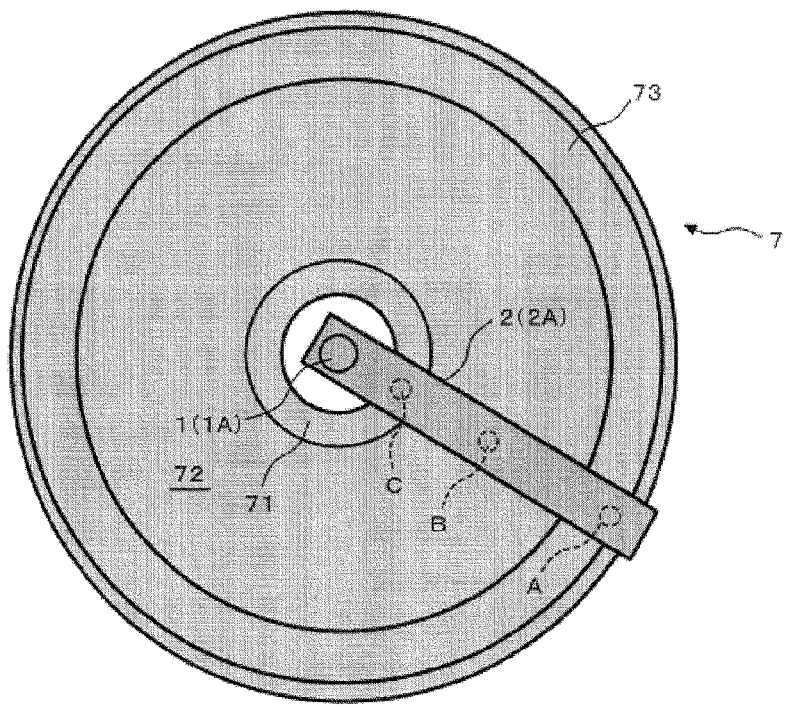

Figure 2B (MAGNETIC FLUX DENSITY OF MAGNETIC FLUX EXTENDING IN CIRCUMFERENTIAL DIRECTION OF WHEEL)

|  | REGION A | REGION B | REGION C |
|---|---|---|---|
| EXAMPLE (AUXILIARY CONDUCTORS, AC 4500A) | 4.2mT | 4.4mT | 8.1mT |
| COMPARATIVE EXAMPLE (NO AUXILIARY CONDUCTORS, DC 6000A) | 0.7mT | 1.5mT | 3.2mT |

Figure 2C (MAGNETIC FLUX DENSITY OF MAGNETIC FLUX EXTENDING IN RADIAL DIRECTION OF WHEEL)

|  | REGION A | REGION B | REGION C |
|---|---|---|---|
| EXAMPLE 1 (7 TURNS, AC 3000A) | 5.9mT | 5.6mT | 5.1mT |
| EXAMPLE 2 (5 TURNS, AC 3000A) | 3.8mT | 4.5mT | 6.8mT |

Figure 3
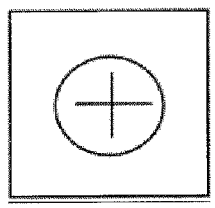
Figure 4A (TEST SPECIMEN PASTED ON PLATE (FRONT SURFACE) CLOSER TO RIM)
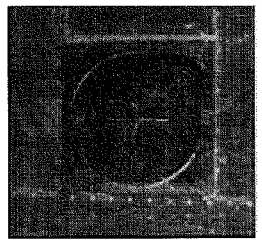
Figure 4B (TEST SPECIMEN PASTED ON PLATE (FRONT SURFACE) CLOSER TO HUB)
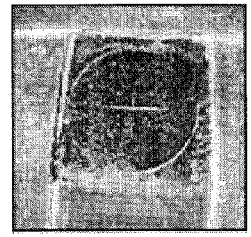
Figure 4C (TEST SPECIMEN PASTED ON PLATE (BACK SURFACE) CLOSER TO RIM)
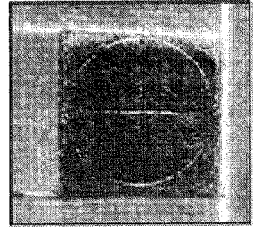
Figure 4D (TEST SPECIMEN PASTED ON PLATE (BACK SURFACE) CLOSER TO HUB)
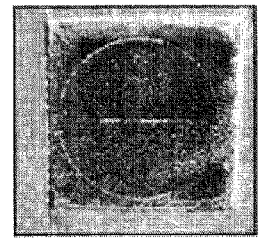

MAGNETIZING APPARATUS FOR MAGNETIC PARTICLE TESTING OF A WHEEL USING A CONDUCTOR AND AUXILIARY CONDUCTORS FOR MAGNETIZATION

TECHNICAL FIELD

The present invention relates to a magnetizing apparatus for magnetic particle testing of a wheel. Particularly, the present invention relates to a magnetizing apparatus for magnetic particle testing capable of sufficiently securing magnetic flux density of a magnetic flux extending in the circumferential direction of the wheel in space in the vicinity of each side surface of the wheel, across the wheel from a hub to a rim thereof.

BACKGROUND ART

A magnetic particle testing method has been widely applied as a conventional quality assurance technique for a railway wheel (referred to simply as a wheel, hereinafter) including a hub, a plate, and a rim in sequence from inward to outward in the radial direction of the wheel.

As a magnetic particle testing apparatus for magnetic particle testing on a wheel, an apparatus disclosed in Patent Literature 1 has been known, for example.

The magnetic particle testing apparatus disclosed in Patent Literature 1, for the purpose of enabling to detect defects in any direction of the entire surface of the wheel, includes: a through conductor inserted into a bore (a hole of hub), and energized with direct current; and a pair of magnetizing coils so disposed as to face respective opposite side surfaces of the wheel, and energized with alternating current.

According to the magnetic particle testing apparatus disclosed in Patent Literature 1, the energized through conductor generates a magnetic flux extending in the circumferential direction of the wheel, which enables radial defects radially extending around the bore to be detected. In addition, each magnetizing coil generates a magnetic flux extending in the radial direction of the wheel, which enables circumferential defects concentrically extending around the bore to be detected.

In Patent Literature 1, defect detectability is evaluated using an A-type standard test specimen specified by JIS, and it is shown that magnetic particle patterns have been clearly observed.

Meanwhile, in Europe, BN918277 and EN13262 are known as manufacturing standards for a railway wheel. In BN918277, the magnetic flux density in space in the vicinity of each side surface of a wheel in a magnetized state is required to be 2.5 mT to 8.2 mT. In EN13262, the magnetic flux density in space in the vicinity of each side surface of a wheel in a magnetized state is required to be 4 mT or more.

CITATION LIST

Patent Literature

[Patent Literature 1] JP2003-344359A

SUMMARY OF INVENTION

Technical Problem

According to the magnetic particle testing apparatus disclosed in Patent Literature 1, magnetic particle patterns formed on the standard test specimen can be clearly observed, as described above.

Unfortunately, based on the studies conducted by the present inventors prior to a sales promotion of wheels in Europe, it has been found that the magnetic flux density of the magnetic flux in space in the vicinity of each side surface of the wheel (particularly, the magnetic flux density of the magnetic flux extending in the circumferential direction of the wheel) does not satisfy the above European standards using the magnetic particle testing apparatus disclosed in Patent Literature 1.

An object of the present invention, which has been made in view of the conventional art, is to provide a magnetizing apparatus for magnetic particle testing capable of sufficiently securing magnetic flux density of a magnetic flux extending in the circumferential direction of a wheel in space in the vicinity of each side surface of the wheel, across the wheel from a hub to a rim thereof.

Solution to Problem

In order to solve the above-described problems, the present invention provides a magnetizing apparatus for magnetic particle testing of a wheel that includes a hub, a plate, and a rim in sequence from inward to outward in a radial direction of the wheel, the apparatus comprising: a conductor inserted through a bore; and a pair of auxiliary conductors connected to respective opposite end portions of the conductor, and so disposed as to face respective opposite side surfaces of the wheel, and to extend from the hub to the rim outwardly in a radial direction of the wheel, wherein the pair of auxiliary conductors and the conductor are energized with alternating current.

The magnetizing apparatus for magnetic particle testing of a wheel according to the present invention includes the conductor inserted through the bore, and this conductor is energized with current so as to generate a concentric magnetic flux around the central axis of the conductor. This means that a magnetic flux extending in the circumferential direction of the wheel is generated. The magnetic flux density of the magnetic flux generated by the conductor becomes gradually decreased apart from the conductor (that is, toward the rim).

The magnetizing apparatus for magnetic particle testing of a wheel according to the present invention includes the pair of auxiliary conductors connected to respective opposite end portions of the conductor, and so disposed as to face the respective opposite side surfaces of the wheel, and to extend outwardly in the radial direction of the wheel from the hub to the rim. To be specific, one auxiliary conductor of the pair of auxiliary conductors is connected to one end portion of the conductor, and so disposed as to face one side surface of the wheel, and to extend outwardly in the radial direction of the wheel. The other auxiliary conductor of the pair of auxiliary conductors is connected to the other end portion of the conductor, and so disposed as to face the other side surface of the wheel, and to extend outwardly in the radial direction of the wheel. The pair of auxiliary conductors are energized with current, thereby generating a concentric magnetic flux around the central axis of each auxiliary conductor. As described above, each auxiliary conductor is connected to each end portion of the conductor, and extends outwardly in the radial direction of the wheel, and thus the magnetic flux generated by each auxiliary conductor extends in the circumferential direction of the wheel, and the orientation of this magnetic flux (orientation of the magnetic flux generated between each auxiliary conductor and each side surface of the wheel) is the same as the orientation of the magnetic flux generated by the conductor. Since each auxiliary conductor extends from the hub to the rim of the wheel, the magnetic flux density of the magnetic flux generated by each auxiliary conductor becomes substantially uniform from the hub to the rim of the wheel. Hence, the magnetic flux density of the magnetic flux extending in the circumferential direction of the wheel, which is generated by the conductor and each of the pair of auxiliary conductors, increases as compared with the case of using the conductor alone, and more readily becomes uniform from the hub to the rim of the wheel compared with the case of using the conductor alone. By rotating the wheel in its circumferential direction while magnetizing the wheel, the magnetic flux density of the magnetic flux extending in the circumferential direction of the wheel can be increased in the whole space in the vicinity of each side surface of the wheel, and the magnetic flux density can be readily uniform from the hub to the rim of the wheel.

In the magnetizing apparatus for magnetic particle testing of a wheel, the pair of auxiliary conductors and the conductor are energized with alternating current, so that the magnetic flux can be concentrated in the vicinity of each side surface of the wheel due to the skin effect, thereby enhancing the magnetic flux density in the space in the vicinity of each side surface of the wheel.

As described above, according to the magnetizing apparatus for magnetic particle testing of a wheel of the present invention, the magnetic flux density of the magnetic flux extending in the circumferential direction of the wheel in the space in the vicinity of each side surface of the wheel can be sufficiently secured across the wheel from the hub to the rim thereof.

Preferably, the magnetizing apparatus for magnetic particle testing of a wheel further comprises a pair of magnetizing coils each of which axial centerline direction faces each side surface of the wheel, the magnetizing coils being energized with alternating current.

According to the above preferable configuration, the pair of magnetizing coils energized with alternating current are arranged such that the direction of the axial centerlines thereof face the respective opposite side surfaces of the wheel. To be specific, one magnetizing coil of the pair of magnetizing coils is arranged such that the direction of its axial centerline faces one side surface of the wheel. The other magnetizing coil of the pair of magnetizing coils is arranged such that the direction of its axial centerline faces the other side surface of the wheel. The magnetic flux extending in the radial direction of the wheel is generated by this pair of magnetizing coils.

According to the above preferable configuration, the magnetic flux extending in the circumferential direction of the wheel is generated by the conductor and the pair of auxiliary conductors as described above, and at the same time, the magnetic flux extending in the radial direction of the wheel is generated by the pair of magnetizing coils; therefore, it is possible to detect defects in any direction on each side surface of the wheel.

Advantageous Effects of Invention

According to the present invention, it is possible to sufficiently secure magnetic flux density of a magnetic flux extending in the circumferential direction of a wheel in space in the vicinity of each side surface of the wheel across the wheel from a hub to a rim thereof. Accordingly, it is possible to satisfy Standards BN918277, EN13262 in Europe by appropriately adjusting a current value of alternating current and the like without excessively increasing this value.

BRIEF DESCRIPTION OF DRAWINGS

FIGS. 2A to 2C are diagrams showing an example of results from measurement of magnetic flux density in space in the vicinity of each side surface of the wheel using the magnetizing apparatus for magnetic particle testing shown in FIG. 1.

FIG. 3 is a schematic diagram showing a standard test specimen used for evaluating defect detectability using the magnetizing apparatus for magnetic particle testing shown in FIG. 1.

FIGS. 4A to 4D show examples of magnetic particle patterns adhering on the standard test specimen shown in FIG. 3.

DESCRIPTION OF EMBODIMENT

One embodiment of the present invention will be described with reference to accompanying drawings, hereinafter.

Figure 1A:
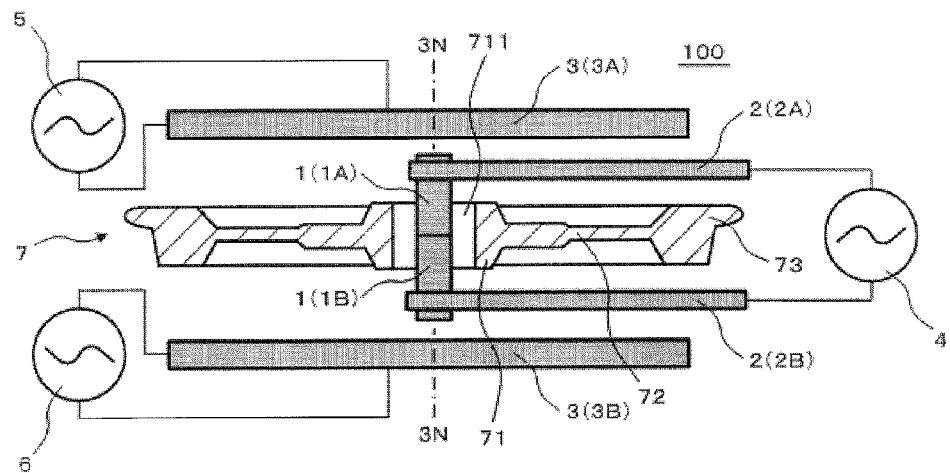
FIGS. 1A and 1B are schematic configuration diagrams showing a wheel in a magnetized state using a magnetizing apparatus for magnetic particle testing according to one embodiment of the present invention.
Figure 1B:
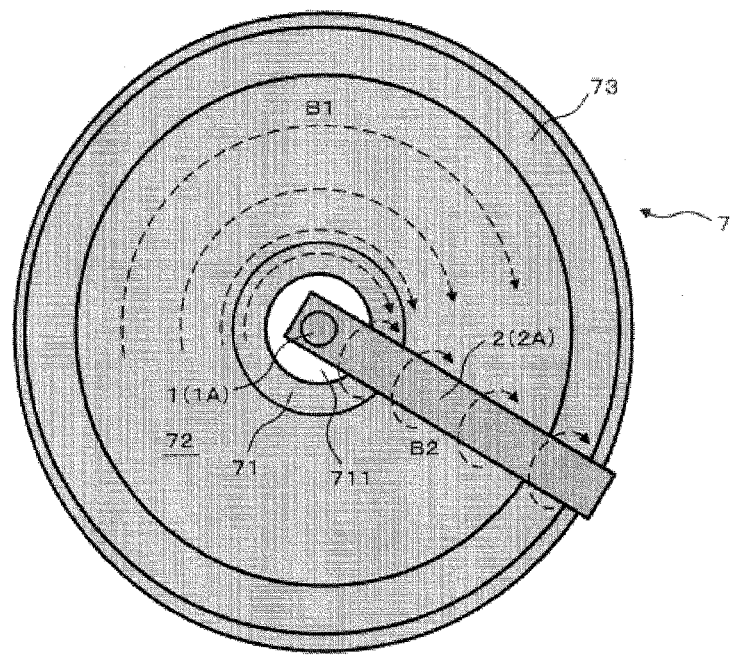

FIGS. 1A and 1B are schematic configuration diagrams showing a wheel in a magnetized state using a magnetizing apparatus for magnetic particle testing according to one embodiment of the present invention. FIG. 1A is a front elevation viewed in a direction orthogonal to an axial direction of the wheel. In FIG. 1A, the wheel is illustrated as its cross section. FIG. 1B is a front elevation viewed in the axial direction of the wheel. In FIG. 1B, magnetizing coils and an AC power supplies are not illustrated in the drawing.

As shown in FIGS. 1A and 1B, the magnetizing apparatus for magnetic particle testing (also referred to simply as the "magnetizing apparatus", hereinafter) 100 according to the present embodiment is a magnetizing apparatus for magnetic particle testing of the wheel 7 including a hub 71, a plate 72, and a rim 73 in sequence from inward to outward in the radial direction of the wheel 7.

The magnetizing apparatus 100 includes a conductor 1, and a pair of auxiliary conductors 2 (2A, 2B) connected to respective opposite end portions of the conductor 1. The magnetizing apparatus 100 also includes an AC power supply 4 connected to the respective auxiliary conductors 2A, 2B.

The conductor 1 is formed of copper, for example, and inserted through a bore (hole through which an axle is inserted) 711 formed in the hub 71 of the wheel 7. The conductor 1 of the present embodiment includes a pair of cylindrical conductor pieces 1A, 1B, and each of the conductor pieces 1A, 1B is inserted into the bore 711 from each side surface of the wheel 7 (side surface in an orthogonal direction to the axial direction of the wheel 7) so that each opposite end portion of the conductor pieces 1A, 1B is put into a state of butting each other.

Alternating current is supplied to each of the auxiliary conductors 2A, 2B from the AC power supply 4, thereby energizing the conductor 1 with the alternating current.

The conductor 1 is energized with the alternating current, thereby generating a magnetic flux B1 concentric around the central axis of the conductor 1. This means that the magnetic flux B1 extending in the circumferential direction of the wheel 7 is generated. The magnetic flux density of the magnetic flux B1 generated by the conductor 1 becomes gradually decreased apart from the conductor 1 (that is, toward the rim 73).

The magnetic flux B1 shown in FIG. 1B indicates a magnetic flux formed in a state where current flows from this side to the other side in the perpendicular direction to the paper plane.

The pair of auxiliary conductors 2 are formed of copper, for example, and connected to the respective opposite end portions of the conductor 1, as aforementioned. Specifically, in the present embodiment, one auxiliary conductor 2A is connected to an end portion (end portion not in contact with the conductor piece 1B) of one conductor piece 1A, and the other auxiliary conductor 2B is connected to an end portion (end portion not in contact with the conductor piece 1A) of the other conductor piece 1B. The pair of auxiliary conductors 2 of the present embodiment are configured to be long tabular members, and so disposed as to face the respective opposite side surfaces of the wheel 7, and to extend outwardly in the radial direction of the wheel 7 from the hub 71 to the rim 73.

In the present embodiment, the auxiliary conductors 2A, 2B are arranged substantially at the identical position when viewed from the axial direction of the wheel 7, but the present invention is not limited to this. For example, the auxiliary conductor 2A and the auxiliary conductor 2B may be orthogonally arranged to each other when viewed from the axial direction of the wheel 7, or the auxiliary conductor 2A and the auxiliary conductor 2B may be arranged such that their extending directions are opposite to each other.

Each end portion of the auxiliary conductors 2A, 2B is supplied with alternating current from the AC power supply 4 so as to energize each of the auxiliary conductors 2A, 2B with the alternating current. Each of the auxiliary conductors 2A, 2B is energized with the alternating current, thereby generating the magnetic flux B2 concentric around each central axis of the auxiliary conductors 2A, 2B. As aforementioned, the auxiliary conductors 2A, 2B are connected to the respective end portions of the conductor 1, and also extend outwardly in the radial direction of the wheel 7; therefore, the magnetic flux B2 generated by each of the auxiliary conductors 2A, 2B extends in the circumferential direction of the wheel 7, and the orientation of the magnetic flux B2 (orientation of the magnetic flux B2 generated between each auxiliary conductor 2 and each side surface of the wheel 7) is the same as the orientation of the magnetic flux B1 generated by the conductor 1. Since each of the auxiliary conductors 2A, 2B extends from the hub 71 to the rim 73 of the wheel 7, the magnetic flux density of the magnetic flux B2 generated by each of the auxiliary conductors 2A, 2B becomes substantially uniform from the hub 71 to the rim 73 of the wheel 7.

The magnetic flux B2 shown in FIG. 1B is illustrated as a magnetic flux generated in a state where the current flows in the auxiliary conductor 2A in the direction from the rim 73 to the hub 71 (state where the current flows to the conductor 1 in the direction from this side to the other side in the perpendicular direction to the paper plane).

Hence, the magnetic flux density of the magnetic flux (magnetic flux formed by superimposing the magnetic fluxes B1, B2) extending in the circumferential direction of the wheel 7, which is generated by the conductor 1 and the pair of auxiliary conductors 2, increases as compared with the case of using the conductor 1 alone, and more readily becomes uniform from the hub 71 to the rim 73 of the wheel 7 compared with the case of using the conductor 1 alone. By rotating the wheel 7 in its circumferential direction while magnetizing the wheel 7, the magnetic flux density of the magnetic flux extending in the circumferential direction of the wheel 7 can be increased in the whole space in the vicinity of each side surface of the wheel 7, and the magnetic flux density can be readily uniform from the hub 71 to the rim 73 of the wheel 7.

In the magnetizing apparatus 100, the pair of auxiliary conductors 2 and the conductor 1 are energized with alternating current, so that the magnetic flux can be concentrated in the vicinity of each side surface of the wheel 7 due to the skin effect, thereby enhancing the magnetic flux density in the space in the vicinity of each side surface of the wheel 7.

As described above, according to the magnetizing apparatus 100 of the present embodiment, the magnetic flux density of the magnetic flux extending in the circumferential direction of the wheel 7 in the space in the vicinity of each side surface of the wheel 7 can be sufficiently secured across the wheel 7 from the hub 71 to the rim 73.

As a preferable configuration, the magnetizing apparatus 100 according to the present embodiment may include a pair of magnetizing coils 3 (3A, 3B) arranged such that the direction of their axial centerlines 3N face the respective opposite side surfaces of the wheel 7. To be specific, each of the magnetizing coils 3A, 3B is formed of a conducting wire wound around the axial centerline 3N opposite to each side surface of the wheel 7, and the axial centerline 3N is arranged to be substantially coaxial with the axle of the wheel 7. The magnetizing apparatus 100 includes an AC power supply 5 connected to the magnetizing coil 3A, and an AC power supply 6 connected to the magnetizing coil 3B.

Alternating current is supplied to the magnetizing coil 3A from the AC power supply 5 so as to energize the magnetizing coil 3A with the alternating current, thereby generating a magnetic flux extending in the radial direction of the wheel 7 (magnetic flux radially extending around the axle of the wheel 7). In the same manner, alternating current is supplied to the magnetizing coil 3B from the AC power supply 6 so as to energize the magnetizing coil 3B with the alternating current, thereby generating a magnetic flux extending in the radial direction of the wheel 7.

According to the magnetizing apparatus 100 of the present embodiment, as aforementioned, not only the magnetic flux extending in the circumferential direction of the wheel 7 is generated by the conductor 1 and each of the pair of auxiliary conductors 2, but also the magnetic flux extending in the radial direction of the wheel 7 is generated by each of the pair of magnetizing coils 3; therefore, it is possible to detect defects in any direction of the opposite side surfaces of the wheel 7.

EXAMPLE

Example of the present invention will be described, hereinafter.

A magnetic flux density measurement test was conducted in which the wheel 7 was magnetized using the magnetizing apparatus 100 having the aforementioned configuration, and during the magnetizing, the magnetic flux density in the space in the vicinity of each side surface of the wheel 7 (the magnetic flux density of the magnetic flux extending in the circumferential direction of the wheel 7, and the magnetic flux density of the magnetic flux extending in the radial direction of the wheel 7) was measured.

Specifically, alternating current was supplied to each of the auxiliary conductors 2A, 2B from the AC power supply 4 so as to energize the auxiliary conductors 2A, 2B and the conductor 1 with the alternating current, and at this time, the magnetic flux density of the magnetic flux extending in the circumferential direction of the wheel 7 was measured.

Subsequently, after the supply of the alternating current from the AC power supply 4 was stopped, alternating current was supplied to the magnetizing coil 3A from the AC power supply 5, and alternating current was also supplied to the magnetizing coil 3B from the AC power supply 6 so as to energize the magnetizing coils 3A, 3B with the alternating current, and at this time, the magnetic flux density of the magnetic flux extending in the radial direction of the wheel 7 was measured.

As Comparative Example of the present invention, a magnetic flux density measurement test was conducted in which the pair of auxiliary conductors 2 were omitted in the same manner as the apparatus disclosed in the above-mentioned Patent Literature 1, and direct current was supplied to the conductor 1 from the DC power supply so as to energize the conductor 1 with the direct current, and at this time, the magnetic flux density of the magnetic flux extending in the circumferential direction of the wheel 7 was measured.

In the measurement of the magnetic flux density in Example and Comparative Example, Deutrometer of Nihon Matech Corporation was used.

FIGS. 2A to 2C are diagrams showing an example of results from measurement of magnetic flux density in the test as described above. FIG. 2A is a diagram for explaining regions (A, B, C) where the magnetic flux density was measured. In FIG. 2A, the region denoted by a reference character A is a spatial region between the rim 73 of the wheel 7 and the auxiliary conductor 2A. The region denoted by a reference character B is a spatial region between the plate 72 (center of the plate 72) of the wheel 7 and the auxiliary conductor 2A. The region denoted by a reference character C is a spatial region between the hub 71 of the wheel 7 and the auxiliary conductor 2A. FIG. 2B shows a result from the measurement of the magnetic flux density of the magnetic flux extending in the circumferential diction of the wheel 7 at the respective regions shown in FIG. 2A. FIG. 2C shows a result from the measurement of the magnetic flux density of the magnetic flux extending in the radial diction of the wheel 7 at the respective regions shown in FIG. 2A.

As shown in Example of FIG. 2B, it was found that, in the magnetizing apparatus 100 according to the present embodiment, through energizing of each auxiliary conductor 2 and the conductor 1 with alternating current of 4500 A, the magnetic flux density of the magnetic flux extending in the circumferential direction of the wheel 7 satisfies 2.5 mT to 8.2 mT specified by Standard BN918277 at all the region A (spatial region in the vicinity of the rim 73), the region B (spatial region in the vicinity of the plate 72), and the region C (spatial region in the vicinity of the hub 71). It was also found that the magnetic flux density of the magnetic flux extending in the circumferential direction of the wheel 7 satisfies 4 mT or more specified by Standard EN13262 at all the region A to the region C.

To the contrary, as shown in Comparative Example of FIG. 2B, in the case of merely energizing the conductor 1 with direct current, although the current value was set to be as great as 6000 A, the magnetic flux density of the magnetic flux extending in the circumferential direction of the wheel 7 satisfies Standard BN918277 only at the region C. The magnetic flux density of the magnetic flux extending in the circumferential direction of the wheel 7 does not satisfy Standard EN13262 at any of the region A to the region C.

If it is possible to increase the current value used for energizing the conductor 1 by approximately six times (36000 A), the magnetic flux density of the magnetic flux extending in the circumferential direction of the wheel 7 may satisfy Standard EN13262 at all the region A to the region C. It is, however, very likely that Standard BN918277 is not satisfied at the region C because the magnetic flux density becomes excessively great.

As described above, according to the magnetizing apparatus 100 of the present embodiment, the magnetic flux is generated by the conductor 1 and the pair of auxiliary conductors 2, so that the magnetic flux density can be increased with smaller current compared with the case of using the conductor 1 alone, and can be more readily uniform from the hub 71 to the rim compared with the case of using the conductor 1 alone. Accordingly, it is possible to relatively easily satisfy Standard BN918277 and Standard EN13262.

As shown in Example 2 of FIG. 2C, it was found that, using the magnetizing coils 3 of five turns in the magnetizing apparatus 100 according to the present embodiment, and through energizing of the magnetizing coils 3 with alternating current of 3000 A, the magnetic flux density of the magnetic flux extending in the radial direction of the wheel 7 can satisfy 2.5 mT to 8.2 mT specified by Standard BN918277 at all the region A, the region B, and the region C. At the region A, however, the magnetic flux density of the magnetic flux extending in the radial direction of the wheel 7 is slightly insufficient for 4 mT or more specified by Standard EN13262.

For this reason, as shown in Example 1 of FIG. 2C, the intensity of magnetization was enhanced by increasing the number of turns of each magnetizing coil 3 to seven from five; and as a result, it was found that the magnetic flux density of the magnetic flux extending in the radial direction of the wheel 7 satisfies both Standard BN918277 and Standard EN13262 at all the region A to the region C.

While magnetizing the wheel 7 using the magnetizing apparatus 100 according to the present embodiment, a defect detectability evaluation test was also conducted using a standard test specimen specified by ASTM (ASTM CX-230) as shown in FIG. 3. FIGS. 4A to 4D show examples of magnetic particle patterns adhering on the standard test specimen, which were observed in this test.

According to the magnetizing apparatus 100 of the present embodiment, as aforementioned, the magnetic flux density can be increased with smaller current compared with the prior art using the conductor 1 alone, and it is possible to obtain the magnetic flux density more uniform from the hub 71 to the rim 73 compared with the prior art using the conductor 1 alone. Accordingly, it was confirmed that magnetic particle patterns as clear as, or more clear than those in the prior art could be observed.

REFERENCE SIGNS LIST

1 Conductor
1A, 1B Conductor piece
2, 2A, 2B Auxiliary Conductor
3, 3A, 3B Magnetizing coil
4, 5, 6 AC power supply
7 Wheel
71 Hub
72 Plate
73 Rim
100 Magnetizing apparatus for magnetic particle testing
711 Bore

The invention claimed is:

1. A magnetizing apparatus for magnetic particle testing of a wheel that includes a hub, a plate, and a rim in sequence from inward to outward in a radial direction of the wheel, the apparatus comprising:
a conductor inserted through a bore of the hub; and
a pair of auxiliary conductors connected to respective opposite end portions of the conductor, and so disposed as to face respective opposite side surfaces of the wheel, and to extend from the hub to the rim outwardly in a radial direction of the wheel,
wherein
the pair of auxiliary conductors and the conductor are energized with alternating current, so that a first magnetic flux which extends in a circumferential direction of the wheel is generated by the conductor and a second magnetic flux which extends in a circumferential direction of the wheel and an orientation of which is the same as an orientation of the first magnetic flux is generated by each auxiliary conductor, the wheel being magnetized by the first magnetic flux and the second magnetic flux.

2. The magnetizing apparatus for magnetic particle testing of a wheel according to claim 1, further comprising a pair of magnetizing coils each of which axial centerline direction faces each side surface of the wheel, the magnetizing coils being energized with alternating current.

* * * * *